United States Patent [19]
Bongardt et al.

[11] Patent Number: 6,160,144
[45] Date of Patent: Dec. 12, 2000

[54] SYNTHETIC ESTERS OF ALCOHOLS AND FATTY ACID MIXTURES OF VEGETABLE OILS HIGH IN OLEIC ACID AND LOW IN STEARIC ACID

[75] Inventors: Frank Bongardt, Duesseldorf; Britta Bossmann, Erkrath; Alfred Westfechtel, Hilden; Wolfgang Giede, Langenfeld, all of Germany

[73] Assignee: Henkel Kommanditgesellschaft auf Aktien, Dusseldorf, Germany

[21] Appl. No.: 08/860,246

[22] PCT Filed: Dec. 4, 1995

[86] PCT No.: PCT/EP95/04767

§ 371 Date: Jun. 12, 1997

§ 102(e) Date: Jun. 12, 1997

[87] PCT Pub. No.: WO96/18598

PCT Pub. Date: Jun. 20, 1996

[30] Foreign Application Priority Data

Dec. 12, 1994 [DE] Germany ............................... 44 44 137

[51] Int. Cl.[7] .................................................... C07C 53/00
[52] U.S. Cl. ............................................ 554/223; 554/224
[58] Field of Search ...................................... 554/223, 224

[56] References Cited

U.S. PATENT DOCUMENTS 4,627,192  12/1986  Fick ............................................ 47/58

FOREIGN PATENT DOCUMENTS

| 387399 | 6/1996 | Australia . |
| 0 414 384 | 2/1991 | European Pat. Off. . |
| 0 496 504 | 7/1992 | European Pat. Off. . |
| 22 31 162 | 1/1974 | Germany . |

OTHER PUBLICATIONS

ECT, vol. 9, pp. 795–805, 1980.

J. Amer. Oil. Chem. Soc. 63:8 1062–65 (1986).

*Primary Examiner*—Deborah Carr
*Attorney, Agent, or Firm*—Wayne C. Jaescke; Glenn E. J. Murphy; Steven J. Trzaska

[57] ABSTRACT

The invention pertains to synthetic esters containing a) fatty acid mixtures with an oleic acid content of 85 wt % and a stearic acid content of 0.5 to 2.5 wt %, both relative to the mixture, b) alcohols and c) as desired, polyfunctional carboxylic acids. The invention also relates to hydraulic oils based on these esters, and to the use of the esters as lubricants, as hydraulic oils and in cosmetics.

19 Claims, No Drawings

SYNTHETIC ESTERS OF ALCOHOLS AND FATTY ACID MIXTURES OF VEGETABLE OILS HIGH IN OLEIC ACID AND LOW IN STEARIC ACID

This application is a 371 of PCT/EP95/04767 filed Dec. 4, 1995.

BACKGROUND OF THE INVENTION

1. Field of the Invention

This invention relates to synthetic esters of alcohols and fatty acid mixtures containing at least 85% by weight of oleic acid and 0.5 to 2.5% by weight of stearic acid and to their use as lubricants and hydraulic oils and for cosmetic purposes.

2. Discussion of the Related Art

With the object of improving the yield of renewable raw materials, various oil plants have recently been modified in the composition of their fatty acid mixtures by breeding measures in order to make them more suitable for industrial purposes. Examples include rape, of which the erucic acid content has been lowered, rape with an increased erucic acid content and sunflowers of which the oils have an increased oleic acid content through reduction of their linoleic acid content.

The selective modification of oil plants in order to increase their oleic acid content by reducing their linoleic acid content is described in U.S. Pat. No. 4,627,192. The composition of "high-oleic sunflower oil" is reported, for example, in J. Amer. Oil Chem. Soc. 63, 1062 (1986). The oleic acid content is of the order of 80 to 86% while the content of linoleic acid is between 4 and 8% and the stearic acid content between 3 and 5%.

The fats and oils obtained from vegetable or animal sources are processed to oleochemical raw materials. On account of the C-chain distribution of the fatty acids which is always present in natural fats and oils, mixtures containing fatty acids of a homologous series are obtained instead of pure substances.

Natural triglycerides show such poor stability to hydrolysis or oxidative degradation that they cannot be used as lubricants for many purposes. Synthetic esters of the fatty acid mixtures obtained from them by splitting show superior performance properties.

An important requirement for an ester-based lubricant is a low pour point according to DIN ISO 3016. Esters of trimethylol propane with "oleic acid" represent one possibility of obtaining lubricants of medium viscosity, low cloud point and low pour point. On account of the C chain distribution already mentioned, "oleic acid" is not a pure substance, but a mixture of various fatty acids.

Technical oleic acid is obtained from tallow. To obtain a sufficiently low cloud point, as measured by the method of Deutsche Gesellschaft für Fettforschung D-III 3 [79], special measures have to be taken to purify the fatty acid mixture, i.e. most of the saturated fatty acids are removed by so-called rolling-up separation. The cloud point of the fatty acid mixture is thus reduced to values of 5° C. to 10° C. The mixture consisting, for example, of 67% oleic acid, 12% linoleic acid and 2% stearic acid is marketed under the name of Edenor® TiO5 and, on esterification with trimethylol propane, gives esters with a cloud point of −20° C. and a pour point of −40° C.

Unfortunately, the esters produced by known methods as described above are not entirely satisfactory in regard to their oxidation stability on account of their content of oxidation-sensitive linoleic acid. Their color and odor are also in need of improvement.

Other problems arise through quality fluctuations because animal fats varying widely in origin are used as the raw material source. Experience has shown that this can lead to unpredictable difficulties in maintaining the cloud point and pour point specification.

To avoid these problems, it seems logical to use a raw material with a higher oleic acid content, i.e. the high-oleic sunflower oil described at the beginning.

Unfortunately, the use of a fatty acid mixture of sunflower oil from new plants (oleic acid content around 85%, linoleic acid content around 5%, stearic acid content around 4%, palmitic acid content around 4%) does not produce the required result: the cloud point of the trimethylol propane ester is −10° C. while its pour point is −20° C.

However, the rolling-up process remains confined to fatty acid mixtures which still have a relatively high linoleic acid content. Accordingly, the cloud point of a high-oleic fatty acid mixture from new sunflowers cannot be reduced to 5° C. by rolling-up separation because pure oleic acid already has a melting point of 14° C.

Hydraulic oils generally contain no water. Nevertheless, water can enter hydraulic oil through defects or during long-term operation. This water must not be emulsified in the hydraulic oil, but instead should separate quickly as a second phase. This so-called demulsifying capacity of hydraulic oils is measured in accordance with DIN 51599. The demulsifying capacity of esters based on technical oleic acid is in need of improvement.

SUMMARY OF THE INVENTION

Accordingly, the problem addressed by the present invention was to provide alternative raw materials for the production of esters based on technical oleic acid with which esters of alcohols having safely reproducible low cloud and pour points, a light color, high resistance to oxidation and a high demulsifying capacity could be obtained without any need for the separation of saturated fatty acids.

It has surprisingly been found that fatty acid mixtures from the oil of high-oleic, low-stearic sunflowers are particularly suitable for this purpose and have a number of unexpected advantages, for example in regard to demulsifying capacity.

DESCRIPTION OF THE INVENTION

The present invention relates to synthetic esters containing a) fatty acid mixtures, b) alcohols and c) if desired, polybasic carboxylic acids, in which the fatty acid mixtures contain at least 85% by weight of oleic acid and 0.5 to 2.5% by weight of stearic acid, based on the mixture.

The present invention also relates to the use of the esters for lubricants, hydraulic oils and cosmetic purposes.

It is possible by plant breeding methods to obtain oil plants with a particularly low content of stearic acid, for example the sunflower described in EP-A1 0 496 504 with a content of saturated fatty acids reduced to at most 6% by weight. In one preferred form, the sunflowers according to this patent yield a fatty oil containing 1% by weight or less of stearic acid and no more than 4% by weight of palmitic acid.

In one preferred embodiment of the invention, fatty acid mixtures obtained from this high-oleic, low-stearic sunflower oil are used for the production of esters.

To isolate the fatty acid mixtures, the oil is hydrolyzed under pressure with water in the usual way, the glycerol is removed and the mixture of free acids is isolated.

The fatty acid composition is shown in Table 1.

TABLE 1

Composition of the High-oleic, Low-stearic Sunflower Oil

| Fatty acid component | Content % by weight |
| --- | --- |
| Palmitic acid | 2 to 5 |
| Stearic acid | 0.5 to 2.5 |
| Oleic acid | 85 to 95 |
| Linoleic acid | 2 to 8 |

The fatty acid mixture obtained by hydrolysis of the oil has a composition of at most 6% by weight of saturated fatty acids (palmitic and stearic acid) and preferably 3.6 to 5.0% by weight of saturated fatty acids.

Of these saturated fatty acids, up to at most 2.5% by weight and preferably up to at most 1.5% by weight consist of stearic acid.

If desired, the palmitic acid may be removed by fractional distillation in order further to increase the purity of the oleic acid.

The synthetic esters according to the invention may contain other monofunctional acids in addition to the fatty acid mixtures according to the invention. The content of fatty acid mixtures according to the invention is at least 50% by weight and preferably at least 90% by weight.

So far as the other monofunctional acids are concerned, fatty acid mixtures from other natural raw materials containing 6 to 22 carbon atoms are mentioned in particular. However, branched carboxylic acids containing 6 to 22 carbon atoms, for example 2-ethyl hexanoic acid, isononanoic acid or isostearic acid, may also be used. Aromatic carboxylic acids, such as benzoic acid, are also suitable.

Suitable alcohols are monohydric and polyhydric alcohols.

Suitable monohydric alcohols are aliphatic or cycloaliphatic, saturated or unsaturated alcohols containing 2 to 22 carbon atoms.

Preferred alcohols are n-propanol, i-propanol, n-butanol, i-butanol, hexanol, octanol, decanol, cocofatty alcohol, stearyl alcohol, 2-ethyl hexanol, i-nonanol, i-tridecyl alcohol and oleyl alcohol.

The alcohols described above may be used individually or in the form of mixtures.

Instead of the alcohols, reaction products thereof with alkylene oxides, preferably ethoxylates or propoxylates, may of course also be used. Each hydroxyl group can have been reacted with 1 to 100 moles, preferably 1 to 30 moles and, more preferably, 1 to 10 moles of alkylene oxide.

In one preferred embodiment of the invention, the alcohols are polyhydric alcohols, so-called polyols. Polyols are alcohols which contain more than one hydroxyl group in the molecule.

In one preferred embodiment, the polyols contain 2 to 6 hydroxyl groups. The polyols preferably contain 2 to 12 carbon atoms.

Suitable polyols are, for example, diols, such as ethylene glycol, propane-1,2-diol, propane-1,3-diol, butane-1,4-diol, hexane-1,6-diol, octane-1,8-diol, decane-1,10-diol, octadecane-1,12-diol, diethylene glycol, triethylene glycol or bishydroxymethyl cyclohexane.

Suitable higher polyols are, for example, glycerol, polyglycerol, sorbitol or mannitol.

One particularly preferred embodiment of the invention is characterized by the use of polyols having a so-called neo-structure, i.e. polyols derived from neopentane. Polyols such as these are distinguished by the fact that they do not have any hydrogen at the carbon atoms adjacent the carbon atom carrying the hydroxyl group.

Preferred examples of such polyols are neopentyl glycol, trimethylol ethane, trimethylol propane, ditrimethylol propane, pentaerythritol, dipentaerythritol and tripentaerythritol.

Instead of the polyols, reaction products thereof with alkylene oxides, preferably ethoxylates or propoxylates, may of course also be used. Each free hydroxyl group in the polyol can have been reacted with 1 to 100 moles, preferably with 1 to 30 moles and, more preferably, with 1 to 10 moles of alkylene oxide.

The polyols described above may be used individually or in the form of mixtures. Mixtures of monohydric alcohols and polyols may of course also be used.

In one preferred embodiment, the polyols are completely or almost completely esterified with the fatty acid mixtures according to the invention.

However, partial esters of the polyols mentioned above, in which on average 16 to 80 mole-% of the hydroxyl groups are esterified, also fall within the scope of the invention. Examples of preferred partial esters are glycerol esterified with 1 or 2 moles of a fatty acid mixture according to the invention, trimethylol propane esterified with 1 or 2 moles of a fatty acid mixture according to the invention or pentaerythritol esterified with 1 or 2 moles of a fatty acid mixture according to the invention.

The partial esters according to the invention are distinguished by the fact that the deposits which form with time in partial esters based on technical oleic acid no longer occur or are at least greatly reduced.

Besides the simple esters of the monofunctional fatty acids with the polyols, the complex esters known per se may also be produced by the partial use of polybasic carboxylic acids in the esterification process. The polybasic carboxylic acids are preferably di- and/or tricarboxylic acids containing 2 to 54 carbon atoms.

Preferred polybasic carboxylic acids are, for example, succinic acid, adipic acid, sebacic acid, isomers of phthalic acid or dimer fatty acid. A particularly suitable tribasic carboxylic acid is trimer fatty acid which can be obtained, for example, by working up the distillation residue of dimer fatty acid obtained by dimerization of tall oil fatty acid.

Mixtures of the individual di- and/or tricarboxylic acids may of course also be used.

In the production of the synthetic esters, the equivalent OH:COOH ratio is generally in the range from 1.2:1 to 0.9:1 and preferably in the range from 1.05:1 to 0.95:1 where complete esterification is required.

Where polybasic carboxylic acids are partly used, the equivalent ratio of COOH from polybasic carboxylic acids to COOH from monobasic carboxylic acids is in the range from 0.05 to 0.5:1, preferably in the range from 0.01 to 0.2:1 and more preferably in the range from 0.05 to 0.15:1.

Production may be carried out by the methods normally used for producing esters. For example, the polyols and the fatty acids may be heated with stirring in a reaction vessel to temperatures of 100 to 250° C. until the esterification reaction—accompanied by the elimination of water— begins. Removal of the water can be facilitated by azeotropic removal with an entraining agent or accelerated by passing through an inert gas. To accelerate the esterification reaction, standard catalysts, for example p-toluene sulfonic acid or tin compounds, such as tin oxalate or tin octoate, and also pure tin in the form of tin grindings, may be added. The esterification reaction is generally continued until no more water is separated off.

The esters according to the invention may of course also be produced by a transesterification reaction, for example from the methyl esters of the fatty acids and the polyols with removal of methanol. Standard catalysts, such sodium methylate, zinc soaps or titanium compounds, such as titanium tetraisopropylate, may be added to accelerate the transesterification.

The complex esters may be produced by reacting the polyol, fatty acid and polybasic carboxylic acid in a one-stage reaction. However, the reaction may also be carried out in several stages, for example by initially reacting part or all of the monocarboxylic acid with the polyol and, on completion of this reaction, reacting the remaining hydroxyl groups with the polybasic carboxylic acid or a mixture thereof with residual monocarboxylic acid. The complex esters may also be produced by transesterification.

After their production, the esters according to the invention may if necessary be purified, for example by distilling off impurities, preferably under reduced pressure, by washing with dilute alkali hydroxides or by adsorptive treatments, for example with bleaching earth or with calcium hydroxide.

Hydraulic oils are fluids for hydrostatic power transmission. It has been found that hydraulic oils containing the esters according to the invention, particularly esters based on polyhydric alcohols and, in a particularly preferred embodiment, esters of trimethylol propane, possess particularly good properties.

Accordingly, the present invention also relates to hydraulic oils containing synthetic esters of fatty acid mixtures containing at least 85% by weight of oleic acid and 0.5 to 2.5% by weight of stearic acid, based on the mixture, and alcohols and, if desired, polybasic carboxylic acids.

The hydraulic oils according to the invention contain at least 75% by weight and preferably at least 95% by weight of the esters according to the invention. They may also contain other additives known per se for this particular application, for example antifoam agents, anti-stick-slip additives, corrosion inhibitors, oxidation inhibitors, pour point improvers, anti-wear additives, detergents and/or emulsifiers.

The hydraulic oils may also contain mineral oil in small quantities, although this is preferably not the case.

By virtue of their ready biodegradability, the hydraulic oils are used above all for applications where hydraulic oil is occasionally released into the environment in use, i.e. for example in agricultural machinery.

The synthetic esters according to the invention, preferably those of polyols, may be used as lubricants or as a constituent of lubricants.

The esters according to the invention used as lubricants generally have the following characteristic data: a hydroxyl value of at most 25 and preferably of at most 5, an acid value of at most 2 and preferably of at most 0.5, a pour point of at least −40° C. and a Lovibond 1 inch color value, as determined by the method of the Deutsche Gesellschaft für Fettforschung (DGF) C-V 4b [84], of at most 7 yellow, preferably at most 5 yellow, and at most 1.5 red, preferably at most 0.5 red.

Depending on the requirements which the lubricant is expected to satisfy, its viscosity may assume various values; for esters of trimethylol propane, it is in the range from 40 to 50 mm$^2$/s at 40° C., as measured in accordance with DIN 51562.

Another potential application is in the field of hydraulic oils.

By virtue of their favorable properties in regard to color, odor and low cloud point, the esters according to the invention may also be used for cosmetic purposes, above all as oils.

EXAMPLES

In the following Examples, all percentages are by weight, unless otherwise indicated.

TABLE 2

Comparison of the Fatty Acid Mixture from High-oleic, Low-stearic Sunflowers (Sf$_{HO,LS}$) and Edenor® TiO5:

| | Fatty Acid Mixtures | |
|---|---|---|
| | Sf$_{HO,LS}$ Invention | TiO5 Comparison |
| Palmitic acid | 3.5% | 5% |
| Stearic acid | 1.0% | 1% |
| Oleic acid | 91.0% | 71% |
| Linoleic acid | 4.2% | 11% |
| Cloud point (DGF D-III 3 [79]) | +9° C. | +5° C. |

*The values do not add up to 100% because only the most important fatty acids are mentioned.

It can be seen from the Table that the cloud point of the fatty acid mixture from high-oleic, low-stearic sunflower oil is distinctly higher that in the case of technical oleic acid (Edenor® TiO5).

Esters with trimethylol propane

Example 1 and Comparison Example 1

Esters of trimethylol propane were produced from both fatty acid mixtures.

Procedure

In a reaction vessel equipped with a stirrer, nitrogen inlet and water separator, 2.67 moles trimethylol propane 8.0 moles fatty acid mixture 0.3% by weight tin(II) oxalate, based on the fatty acid mixture, were esterified at temperatures of around 200° C. to 220° C. until no more water was separated off. 1% by weight of bleaching earth (Tonsil), based on the reaction mixture, was then added, after which the reaction mixture was stirred for 10 minutes and filtered.

TABLE 3

Performance Properties of TMP Esters Based on Technical Oleic Acid and the Fatty Acid Mixture from High-oleic, Low-stearic Sunflowers

| Property | Sf$_{HO,LS}$ Invention | TiO5 Comparison |
|---|---|---|
| Viscosity according to DIN 51562, 40° C. | 50 mm$^2$/s | 46 mm$^2$/s |

TABLE 3-continued

Performance Properties of TMP Esters Based on Technical Oleic Acid and the Fatty Acid Mixture from High-oleic, Low-stearic Sunflowers

| Property | Sf$_{HO,LS}$ Invention | TiO5 Comparison |
|---|---|---|
| Viscosity according to DIN 51562, 100° C. | 10 mm$^2$/s | 9.5 mm$^2$/s |
| Viscosity index DIN ISO 2909 | 190 | 180 |
| Cloud point DIN ISO 3015 | −35° C. | −20° C. |
| Pour point DIN ISO 3016 | −50° C. | −40° C. |
| Acid value DIN 53402 | 0.4 | 0.5 |
| Hydroxyl value DIN 53240 | 7 | 7 |
| Color value Lovibond 1 inch DGF C-V 4b [84] | Yellow 3.2 Red 0.4 | Yellow 6.8 Red 1.5 |
| Odor | Neutral | Fatty, slightly rancid |
| Oxidation stability Ranzimat | 13 h | 4.5 h |
| Demulsifying capacity DIN 51381 | 20 mins. | >60 mins. |

Oxidation stability was measured in a Metrohm Ranzimat. The result is expressed as the induction period, i.e. the time elapsing before an increase in conductivity.

Comparison of the performance data shows clear advantages for the esters according to the invention in regard to cloud point, pour point, oxidation stability and demulsifying capacity.

Esters with decyl alcohol

Example 2 and Comparison Example 2

In a stirred reactor equipped with a water separator and nitrogen inlet, 561 g (2 moles) of fatty acid mixture were esterified with 364.6 g (2.3 moles) of a C$_{10-18}$ fatty alcohol mixture (hydroxyl value 354) in the presence of 0.032 g of tin(II) oxide at temperatures of 200 to 220° C. until the acid value had fallen to 0.17. The product was then distilled for purification. It had a boiling point of 226 to 230° C. at 0.1 to 0.09 mbar.

An ester with the following characteristic data is obtained where the fatty acid mixture from high-oleic, low-stearic sunflower oil is used:

Acid value: 0.3, saponification value 131, hydroxyl value 3.5, iodine value 59, cloud point 0 to −1° C.

The ester similarly produced from Edenor® TiO5 has a cloud point of +5° C.

Esters with 2-ethyl hexanol

Example 3 and Comparison Example 3

In a stirred reactor equipped with a water separator and nitrogen inlet, 283.3 g (1 mole) of fatty acid mixture were esterified with 143.2 g (1.1 mole) of 2-ethyl hexanol in the presence of 0.013 g of tin(II) oxide at temperatures of 200 to 220° C. until the acid value had fallen to 0.8. The product was then distilled for purification. It had a boiling point of 167 to 186° C. at 0.1 to 0.09 mbar.

An ester with the following characteristic data is obtained where the fatty acid mixture of high-oleic, low-stearic sunflower oil is used:

Acid value: 0.2, saponification value 142, hydroxyl value 3.7, iodine value 65, cloud point −27° C.

The ester similarly produced from Edenor® TiO5 has a cloud point of −16° C.

Esters with neopentyl glycol

Example 4

In a stirred reactor equipped with a nitrogen inlet and water separator, 425 g (1.5 mole) of a fatty acid mixture from high-oleic, low-stearic sunflower oil were esterified with 87.2 g (0.837 mole) of neopentyl glycol in the presence of 0.05 g of tin(II) oxide at temperatures of 200 to 240° C. until the acid value had fallen to <3. The reaction mixture was then left to react for 3 hours under a vacuum of 20 torr at a temperature of 240° C. For purification, 5.3 g of bleaching earth (Tonsil Standard) were added to the product and the whole was stirred for 1 hour at 90° C. and then filtered.

Complex ester

Example 4

In a stirred reactor equipped with a nitrogen inlet and a water separator, 566.6 g (2 moles) of a fatty acid mixture from high-oleic, low-stearic sunflower oil were esterified with 108.5 g (0.81 mole) of trimethylol propane (98%) and 92.9 g (0.159 mole) of a dimer fatty acid (molecular weight 584.4) in the presence of 0.22 g of tin(II) oxalate at temperatures of 200 to 240° C. until the acid value had fallen to 2. Esterification was then continued for 3 hours under a vacuum of 20 to 2 torr and at a temperature of 240° C. until the acid value had fallen to 0.5.

For purification, 3.2 g of bleaching earth (Tonsil Standard) were added to the product and the whole was stirred for 1 hour at 90° C. and then filtered.

We claim:

1. Synthetic esters of a mixture of fatty acids and an alcohol, wherein the fatty acid mixture comprises at least 85% by weight oleic acid and 0.5% to 2.5% by weight stearic acid, based on the weight of the mixture and wherein the alcohol is a polyol.

2. Esters as claimed in claim 1, wherein the stearic acid content of the fatty acid mixture is between 0.5 and 1.5% by weight, based on the mixture.

3. Esters as claimed in claim 1, comprising at least 50% by weight of the fatty acid mixture.

4. Esters as claimed in claim 1, wherein the polyol contains 2 to 6 hydroxyl groups.

5. Esters as claimed in claim 1, wherein in the polyol, each carbon atom bound to a carbon atom with a hydroxyl group has no hydrogen.

6. Esters as claimed in claim 1, wherein the polyol is selected from the group consisting of neopentyl glycol, trimethylol ethane, trimethylol propane, ditrimethylol propane, pentaerythritol, dipentaerythritol, and tripentaerythritol.

7. Esters as claimed in claim 1, wherein the esters are partial esters in which on average 16 to 80 mole percent of the hydroxyl groups of the polyol are esterified.

8. Synthetic esters of a mixture of fatty acids, an alcohol, and a polybasic carboxylic acid, wherein the fatty acid mixture comprises at least 85% by weight oleic acid and 0.5 to 2.5% by weight stearic acid, based on the weight of the mixture and wherein the alcohol is a polyol.

9. Esters as claimed in claim 8, wherein the polybasic carboxylic acids is a di- or tricarboxylic acid containing 2 to 54 carbon atoms.

10. Esters as claimed in claim 9, wherein the di- or tricarboxylic acid is selected from the group consisting of succinic acid, adipic acid, sebacic acid, isomers of phthalic acid, dimer fatty acid, and trimer fatty acid.

11. Esters as claimed in claim 10, wherein the ratio of OH:COOH equivalents is from 1.2:1 to 0.9:1.

12. Esters as claimed in claim 11, wherein the ratio of OH:COOH equivalents is from 1.05:1 to 0.95:1.

13. Esters as claimed in claim 12, wherein the ratio of COOH from polybasic carboxylic acids to COOH from monobasic carboxylic acids is from 0.005 to 0.5:1.

14. Esters as claimed in claim 13, wherein the ratio of COOH from polybasic carboxylic acids to COOH from monobasic carboxylic acids is from 0.01 to 0.2:1.

15. Esters as claimed in claim 14, wherein the ratio of COOH from polybasic carboxylic acids to COOH from monobasic carboxylic acids is from 0.05 to 0.15:1.

16. Synthetic esters of a mixture of fatty acids and an alcohol, wherein the fatty acid mixture comprises at least 85% by weight oleic acid and 0.5% to 2.5% by weight stearic acid, based on the weight of the mixture, and wherein the fatty acid mixture is derived from high-oleic acid, low-stearic acid sunflower oil seed.

17. Synthetic esters of a mixture of fatty acids and an alcohol, wherein the fatty acid mixture comprises at least 85% by weight oleic acid and 0.5% to 2.5% by weight stearic acid, based on the weight of the mixture, said esters comprising at least 90% by weight of the fatty acid mixture.

18. Synthetic esters of:
   a. a mixture of fatty acids, wherein the mixture comprises at least 85% by weight oleic acid and 0.5% to 2.5% by weight stearic acid, based on the weight of the mixture, and optionally a monofunctional carboxylic acid having 6 to 22 carbon atoms;
   b. an alcohol or an alkylene oxide, wherein the alcohol is a polyhydric alcohol; and optionally
   c. a polybasic carboxylic acid, wherein the polybasic carboxylic acid is a di- or tricarboxylic acid having 2 to 54 carbon atoms.

19. Synthetic esters of:
   a. a mixture of fatty acids, wherein the mixture comprises at least 85% by weight oleic acid and 0.5% to 2.5% by weight stearic acid, based on the weight of the mixture, and optionally a monofunctional carboxylic acid having 6 to 22 carbon atoms;
   b. an alcohol or an alkylene oxide, wherein the alcohol is selected from the group consisting of n-propanol, i-propanol, n-butanol, i-butanol, hexanol, octanol, decanol, cocofatty alcohol, stearyl alcohol, 2-ethyl hexanol, i-nonanol, i-tridecyl alcohol, oleyl alcohol, ethylene glycol, propane-1,2-diol, propane-1,3-diol, butane-1,4-diol, hexane-1,6-diol, octane-1,8-diol, decane-1,10-diol, octadecane-1,12-diol, diethylene glycol, triethylene glycol, bishydroxymethyl cyclohexane, glycerol, polyglycerol, sorbitol, mannitol, neopentyl glycol, trimethylol ethane, trimethylol propane, ditrimethylol propane, pentaerythritol, dipentaerythritol, and tripentaerythritol; and optionally;
   c. a polybasic carboxylic acid selected from the group consisting of succinic acid, adipic acid, sebacic acid, phthalic acid, dimer fatty acid, and trimer fatty acid.

* * * * *